United States Patent [19]

Kuipers et al.

[11] 4,262,017

[45] Apr. 14, 1981

[54] PREPARATION OF A VITAMIN E DRY POWDER

[75] Inventors: Arie Kuipers, Reitmehring; Herbert Becker, Edling; Hubert Tiefenbacher, Leinfelden-Echterdingen; Horst Schumacher, Bobenheim, all of Fed. Rep. of Germany

[73] Assignee: BASF Aktiengesellschaft, Fed. Rep. of Germany

[21] Appl. No.: 38,258

[22] Filed: May 11, 1979

[30] Foreign Application Priority Data

May 22, 1978 [DE] Fed. Rep. of Germany ....... 2822324

[51] Int. Cl.$^3$ .......................................... A61K 31/355
[52] U.S. Cl. ................................................ 424/284
[58] Field of Search ........................................ 424/284

[56] References Cited

U.S. PATENT DOCUMENTS

| | | | |
|---|---|---|---|
| 3,446,899 | 5/1969 | Cavalli et al. | 424/284 |
| 3,608,083 | 9/1971 | Bunnell et al. | 424/284 |
| 3,873,694 | 3/1975 | Kanig | 424/284 |
| 3,914,430 | 10/1975 | Cannalonga et al. | 424/284 |

FOREIGN PATENT DOCUMENTS

| | | | |
|---|---|---|---|
| 50-101519 | 12/1975 | Japan | 424/284 |
| 1147210 | 4/1969 | United Kingdom | 424/284 |

OTHER PUBLICATIONS

Chem. Abst. 60, 7875(e)–Vendt (1960).
Chem. Abst. 87, 172906(n)–Sawai (1977).

*Primary Examiner*—Douglas W. Robinson
*Attorney, Agent, or Firm*—Keil & Witherspoon

[57] ABSTRACT

A vitamin E dry powder, which contains a protein colloid and a disaccharide as carriers, is prepared by dispersing a vitamin E ester in a residual liquor, low in alkaline earth metal ions and rich in lactose, from the production of lactose, in the presence of from 2 to 30% by weight, based on the solids content of the residual liquor, of a caseinate, and spray-drying the dispersion.

The vitamin E dry powder thus prepared is stable, easy to dose and physiologically safe, so that it can be used for any desired purpose.

2 Claims, No Drawings

PREPARATION OF A VITAMIN E DRY POWDER

The present invention relates to the preparation of a vitamin E dry powder which contains casein and lactose.

German Published Application No. 4789/30 h discloses that vitamin dry powders, especially vitamin A dry powders, can be prepared by dispersing a vitamin oil in a solution containing proteins and carbohydrates, and spray-drying the dispersion. This gives vitamin dry powders having a relatively low content of vitamins.

Further, Belgian Patent 589,766 discloses the conversion of vitamins, inter alia mixtures containing vitamin E, into dry powders, using a colloid and a carbohydrate, but an expensive apparatus is required for the spray-drying operation in order to prevent agglomeration of the particles after spray-drying.

Further, U.S. Pat. No. 3,608,083 discloses a spray-drying process which gives products containing up to 60% of vitamin E. However, this requires the use of a special gelatin devoid of gellability and having a molecular weight of from about 9,000 to 11,000.

It is an object of the present invention to provide a process for the preparation of a vitamin E dry powder which has a high content of vitamin E and can be prepared in conventional spray towers, without special apparatus and without special carriers.

It is a further object of the present invention to use, for the process, readily accessible cheap raw materials in the form of dairy by-products, in place of pure carbohydrates.

We have found that these objects are achieved, according to the invention, by a process for the preparation of a vitamin E dry powder containing a protein colloid and a disaccharide, wherein a vitamin E ester is dispersed in a residual liquor, low in alkaline earth metal ions and rich in lactose, from the production of lactose, in the presence of from 2 to 30% by weight, based on the solids content of the residual liquor, of a caseinate, and the dispersion is spray-dried. The process gives a free-flowing vitamin E dry powder which has a pleasant flavor and may be used as an additive for foodstuffs and animal feeds. The dry powder furthermore has good tableting characteristics.

Suitable vitamin E esters are the conventional esters of d- and d,1-α-tocopherol. Specific examples are vitamin E acetate, vitamin E succinate, vitamin E palmitate and vitamin E nicotinate. Amongst these, the acetate is preferred.

The vitamin E ester is used in such amounts that its content in the dry powder is from 10 to 60% by weight. Preferred vitamin E contents in the dry powder prepared according to the invention are from 20 to 50% by weight.

For the purposes of the invention, residual liquors, low in alkaline earth metal ions and rich in lactose, from the production of lactose are essetially solutions, containing lactose, which are obtained from the production of lactose from whey.

The liquor used can, on the one hand, be a solution obtained by removing the whey protein from the whey, concentrating the liquor and reducing the alkaline earth metal ion content, for example by means of electrodialysis; however, it is advantageous to use the residual liquor, predominantly containing lactose, from the recrystallization of crude lactose carried out in order to prepare pure lactose. The residual liquors to be used according to the invention as a rule contain from 10 to 35% by weight of lactose and, apart from 0.05–1.0% by weight of nitrogenous compounds and 0.1–3.0% by weight of mineral salts, only traces of other constituents, all of which, since they originate from milk, are physiologically safe. The said residual liquors, their preparation and processing are described in detail by G. Nemitz in Landwirtschaftliche Forschung, 1976 Symposium Volume, special issue 33/11, pages 300–315.

Suitable colloids to be used according to the invention are, in particular, caseinates; these are obtained by digesting casein with alkaline compounds, for example with sodium or potassium carbonate or citrate. The starting material for the preparation of caseinates is either carefully washed, pre-dehydrated casein chips or dried casein. Digestion with alkali at a controlled pH of from 6 to 7 gives a colloidal solution of about 20% strength, which is dried in a spray dryer or on drying rollers. In contrast to casein, caseinates are water-soluble and therefore particularly suitable for the preparation of the dry powders according to the invention. Frequently, it may be expedient to prepare the caseinates from casein in the wet mix by adding bases.

Specifically, the procedure followed as a rule in preparing the vitamin E dry powders is that the caseinate, preferably sodium caseinate or potassium caseinate, is dissolved in the lactose-containing residual liquor, advantageously whilst maintaining the pH at from 6 to 8. The oily vitamin E acetate is then homogenized in the solution under pressure, using an emulsifier, for example a fatty acid monoglyceride, fatty acid diglyceride or glycerol polyethylene glycol ricinoleate, and the resulting dispersion is spray-dried in a spray tower.

In general, spray-drying is carried out with a drying gas entry temperature of from 100 to 200° C. and exit temperature of from 60 to 110° C., using conventional known equipment, for example a spray dryer provided with a pressure atomizer, centrifugal atomizer or two-material nozzle atomizer. When using a spray dryer having a centrifugal atomizer, atomizing is as a rule carried out at from 10,000 to 25,000 rpm.

The choice of the amount of caseinate to use depends on the content of vitamin E in the dry powder to be prepared. Thus, if a dry powder having a high vitamin E acetate content, for example 50% by weight, is to be prepared, the caseinate content is from 3 to 30% by weight, based on the dry powder, whilst in the case of the preparation of a dry powder having a relatively low content of vitamin E acetate, for example 25% by weight, the content of caseinate is from 2 to 20% by weight, based on the dry powder. The remainder is in each case essentially lactose. In addition to vitamin E, caseinate and lactose, the dry powders according to the invention may contain other materials, for example other vitamins, other active ingredients desirable in foodstuffs and animal feeds, and, where appropriate, conventional technical auxiliaries, for example flow improvers, eg. synthetic silica (cf. "Synthetische Kieselsäure als Hilfsstoff in der Futtermittelindustrie" Kraftfutter 53 (1970), 436–450).

EXAMPLE 1

59.5 kg of casein are dispersed, at 60–65° C., in 1,000 kg of lactose residual liquor from the production of lactose, the liquor having a solids content of 27%. The pH is brought to 6.5 by adding 10% strength sodium hydroxide solution. 418 kg of vitamin E acetate (containing 93.6% of d,1-α-tocopherol acetate, as determined by gas chromatography), 25 kg of a fatty acid monoglyceride, and the solution obtained above are homogenized together by means of a pressure homogenizer, at 120 bars. The vitamin dispersion thus obtained is dried in a nozzle spray dryer, with a drying air entry temperature of 170° C. and exit temperature of 90° C.; the residual moisture content of the product is 1.1%. During the spraying process, about 1% of amorphous silica, based on the solids content of the product, is introduced continuously in order to improve the flow. 753 kg of a product are obtained, having a vitamin E content of 50.7% as determined by gas chromatography.

EXAMPLE 2

23 kg of casein are dispersed, at 60–65° C., in 1,000 kg of lactose residual liquor having a solids content of 27%. The pH is brought to 6.5 by adding 10% strength sodium hydroxide solution. 116 kg of vitamin E acetate (containing 93.6% of d,1-α-tocopherol acetate, as determined by gas chromatography) and 7 kg of a fatty acid monoglyceride are homogenized with the solution, as described in Example 1, and the product is spray-dried to give a residual moisture content of 2.1%. 408 kg of a dry powder are obtained, containing 26% of vitamin E acetate, as determined by gas chromatography.

EXAMPLE 3

82 kg of casein are dispersed, at 60–65° C., in 1,000 kg of lactose residual liquor having a solids content of 27%. The pH is brought to 6.5 by adding 10% strength sodium hydroxide solution. 138 kg of vitamin E acetate (containing 93.6% of d,1-α-tocopherol acetate, as determined by gas chromatography) and 8.5 kg of a fatty acid monoglyceride are homogenized with the solution, as described in Example 1, and the product is spray-dried to give a residual moisture content of 1.6%. 515 kg of a dry powder are obtained, containing 25.1% of vitamin E acetate, as determined by gas chromatography.

We claim:

1. A process for preparing a vitamin E powder containing from 10 to 60% by weight of vitamin E acetate which process consists essentially of
   (a) dissolving sodium or potassium caseinate in a residual liquor from the production of lactose, which liquor contains from 10 to 35% by weight lactose and, apart from 0.5 to 1.0% by weight of nitrogenous substances and from 0.1 to 3.0% by weight of mineral salts, only traces of other constituents originating from milk, the amount of caseinate in said solution being from 2 to 30% by weight;
   (b) mixing oily vitamin E acetate and said solution in a pressure homogenizer whereby a dispersion of vitamin E acetate in said solution is formed, the amount of vitamin E acetate mixed with the solution being sufficient to produce a final product containing from 10 to 60% by weight of vitamin E acetate; and thereafter
   (c) spray-drying the dispersion to form a powder containing lactose, sodium or potassium caseinate and vitamin E acetate.

2. The process of claim 1, wherein the caseinate is dissolved in the lactose-rich residual liquor while maintaining the pH at from 6 to 8.

* * * * *